(12) United States Patent
Iizuka et al.

(10) Patent No.: US 11,696,975 B2
(45) Date of Patent: Jul. 11, 2023

(54) HYDROGEL

(71) Applicant: SEKISUI PLASTICS CO., LTD., Osaka (JP)

(72) Inventors: Ryo Iizuka, Ibaraki (JP); Kazuki Kato, Ibaraki (JP)

(73) Assignee: SEKISUI PLASTICS CO., LTD., Osaka (JP)

(*) Notice: Subject to any disclaimer, the term of this patent is extended or adjusted under 35 U.S.C. 154(b) by 1107 days.

(21) Appl. No.: 16/338,308

(22) PCT Filed: Sep. 22, 2017

(86) PCT No.: PCT/JP2017/034268
§ 371 (c)(1),
(2) Date: Mar. 29, 2019

(87) PCT Pub. No.: WO2018/062030
PCT Pub. Date: Apr. 5, 2018

(65) Prior Publication Data
US 2020/0016300 A1   Jan. 16, 2020

(30) Foreign Application Priority Data

Sep. 30, 2016 (JP) .................................. 2016-193679
Feb. 23, 2017 (JP) .................................. 2017-031855

(51) Int. Cl.
*A61L 31/14* (2006.01)
*A61L 31/04* (2006.01)
(Continued)

(52) U.S. Cl.
CPC ........... *A61L 31/145* (2013.01); *A61L 31/041* (2013.01); *B32B 27/18* (2013.01); *B32B 27/306* (2013.01);
(Continued)

(58) Field of Classification Search
None
See application file for complete search history.

(56) References Cited

U.S. PATENT DOCUMENTS 6,038,464 A   3/2000 Axelgaard et al.
6,198,955 B1   3/2001 Axelgaard et al.
(Continued)

FOREIGN PATENT DOCUMENTS

CA   2319361   8/1999
CN   1946826 A   4/2007
(Continued)

OTHER PUBLICATIONS

Machine translation of JP 2000-212074 A (Year: 2000).*
(Continued)

*Primary Examiner* — Ramsey Zacharia
(74) *Attorney, Agent, or Firm* — Greenblum & Bernstein, P.L.C.

(57) ABSTRACT

A hydrogel 1 having a laminate structure of layer A 10 and layer B 20, wherein layer A 10 contains a monomer-derived component, water, a humectant, a water-insoluble polymer having tackiness and an amphiphilic polymer, the water-insoluble polymer is contained in a proportion of 3 to 20 wt % based on a total amount of layer A, and the amphiphilic polymer is a polyvinyl alcohol having a saponification degree of 50 to 75% and is contained in a proportion of 0.05 to 5 wt % based on the total amount of layer A; layer B 20 contains a monomer-derived component, water and a humectant and is substantially free of a water-insoluble polymer having tackiness and a polyvinyl alcohol; and an amount of the water based on a total amount of layer B is the amount of water based on the total amount of layer A±10 wt %.

7 Claims, 1 Drawing Sheet

(51) Int. Cl.

| | | |
|---|---|---|
| *B32B 27/18* | (2006.01) | |
| *B32B 27/30* | (2006.01) | |
| *C08F 222/38* | (2006.01) | |
| *C08J 3/075* | (2006.01) | |
| *C09J 7/30* | (2018.01) | |
| *C09J 11/04* | (2006.01) | |
| *C09J 11/06* | (2006.01) | |
| *A61B 5/259* | (2021.01) | |
| *A61B 5/296* | (2021.01) | |
| *A61B 5/398* | (2021.01) | |
| *A61B 18/16* | (2006.01) | |
| *A61B 18/00* | (2006.01) | |
| *A61N 1/04* | (2006.01) | |
| *A61B 5/291* | (2021.01) | |

(52) U.S. Cl.
CPC ........... *C08F 222/385* (2013.01); *C08J 3/075* (2013.01); *C09J 7/30* (2018.01); *C09J 11/04* (2013.01); *C09J 11/06* (2013.01); *A61B 5/259* (2021.01); *A61B 5/291* (2021.01); *A61B 5/296* (2021.01); *A61B 5/398* (2021.01); *A61B 18/16* (2013.01); *A61B 2018/00601* (2013.01); *A61B 2562/0215* (2017.08); *A61B 2562/0217* (2017.08); *A61N 1/0428* (2013.01); *A61N 1/0456* (2013.01); *C08J 2335/00* (2013.01); *C08J 2435/00* (2013.01)

(56) References Cited

U.S. PATENT DOCUMENTS

| | | | |
|---|---|---|---|
| 7,868,072 | B2 | 1/2011 | Sasahara et al. |
| 2007/0208130 | A1 | 9/2007 | Sasahara et al. |

FOREIGN PATENT DOCUMENTS

| | | |
|---|---|---|
| JP | 2000-212074 | 8/2000 |
| JP | 2002-080809 | 3/2002 |
| JP | 2003-335805 | 11/2003 |
| JP | 2003-336024 | 11/2003 |
| JP | 4384809 | 12/2009 |
| JP | 4522405 | 8/2010 |
| JP | 2015-003977 | 1/2015 |
| TW | I306887 | 3/2009 |
| WO | 2005/103186 | 11/2005 |

OTHER PUBLICATIONS

International Search Report issued in International Patent Application No. PCT/JP2017/034268, dated Dec. 19, 2017.

International Preliminary Report on Patentability issued in International Patent Application No. PCT/JP2017/034268, dated Apr. 2, 2019.

The extended European Search Report, European Patent Office, Application No. 17855984.5, dated Mar. 23, 2020.

* cited by examiner

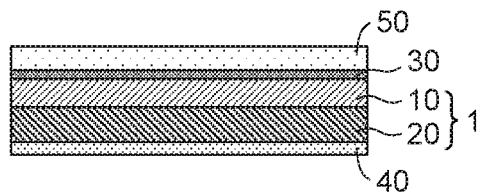

HYDROGEL

TECHNICAL FIELD

The present invention relates to a hydrogel. Particularly, it relates to a hydrogel in a medical electrode which is attached to a living body for use.

BACKGROUND ART

In a medical electrode used for obtaining electrocardiogram and applying a treatment using electric stimulation provided by low-frequency wave, medium frequency wave, etc. an adhesive material of a hydrogel (medical-electrode hydrogel) is used at the portion at which the medical electrode is attached to a living body. The hydrogel is placed between an electrode constituted of a conductive material and the skin surface. As the conductive material, carbon, various metals, Ag—AgCl (silver/silver chloride), etc. are used. In such a medical-electrode hydrogel, when the adhesive force of the gel at the portion (electrode side) in contact with an element is compared to that at the portion in contact with the skin, the adhesive force is usually desirably higher on the electrode side.

As a conventional medical-electrode hydrogel, Patent Literature 1 discloses an electrode containing a conductive member having a means connecting to an external electrical device and a multilayer means electrically connecting the patient's skin and the conductive member, for providing an electrical interface on the patient's skin. According to the description, the multilayer means has a first-layer means, which contains an electrically conductive gel having a relatively low peel strength for enabling detachable contact with patient's skin, and a second-layer means, which contains an electrically conductive gel having a relatively high peel strength for making contact with a conductive member; the first layer means and the second layer means are laminated with a third gel interposed therebetween; the first layer of multiple gel-layers has sufficient adhesiveness by which the electrode can be detachably attached to the patient's skin and the second layer of the multiple gel-layers has adhesiveness by which the multilayer means is permanently attached to the conductive member.

However, the hydrogel is not constantly in contact with the object when used, electricity cannot be stably applied to an object. In contrast, the hydrogel constituting a medical electrode absorbs moisture ascribed to sweat and a moisture content derived from a living body and a moisture content derived from an environment, with the result that adhesiveness sometimes decreases. Because of this, in a conventional medical-electrode hydrogel, the adhesiveness of an electrode element and a hydrogel became insufficient in some cases. In such a case, the electrode element and the hydrogel separated and the electrode element exposed was sometimes in contact with the skin. Also, in the gel layers in Patent Literature 1 mentioned above, there is a risk that adhesiveness decreases under influence of sweat and moisture, depending on the use environment and the hydrogel is removed.

Patent Literature 2 discloses a gel adhesive composition (hydrogel), which contains a crosslinked water-soluble polymer, water, a humectant, a water-insoluble polymer having tackiness and an amphiphilic polymer, in which the amphiphilic polymer is contained in a proportion of 0.05 to 7.0 wt % based on the total amount of the composition except water, and the amphiphilic polymer is selected from a vinyl pyrrolidone/vinyl acetate copolymer containing a hydrophilic group and a hydrophobic group in a ratio (molar ratio) of 1:1 to 3:1, a vinyl pyrrolidone/alkyl acrylate copolymer containing a hydrophilic group and a hydrophobic group in a ratio (molar ratio) of 1:1 to 3:1, and a polyvinyl alcohol having a saponification degree of 50 to 75%. In the hydrogel, a hydrophobic polymer is added to provide initial tack (adhesive force) and ensure tackiness and adhesiveness to an electrode element and an object. The hydrophobic polymer has a satisfactory affinity to an electrode element and viscosity can be enhanced. However, if the hydrogel mentioned above is continuously attached to the skin for a long-term, the adhesive force excessively increased in some cases.

CITATION LIST

Patent Literature

Patent Literature 1: JP Patent No. 4384809
Patent Literature 2: JP Patent No. 4522405

SUMMARY OF INVENTION

Technical Problem

In consideration of the circumstances of the conventional art, the present invention is directed to providing a hydrogel, which is excellent in adhesiveness to an electrode element, less reduced in tackiness and adhesiveness to an electrode element and an object even if it absorbs water such as sweat and moisture, as well as has an optimal adhesive force to the skin surface and gives no damage to the skin when removed.

Solution to Problem

The present inventors have conducted intensive studies and as a result, selected a highly adhesive gel containing a hydrophobic polymer (water-insoluble polymer) and a polyvinyl alcohol as an amphiphilic polymer, for use on the side facing an electrode element, and selected a gel having an optimal adhesive force to the skin, for use on the side facing the skin, in consideration of adhesion property of the skin and the highly adhesive gel; and found that the aforementioned problems are solved by laminating these gels. Based on the findings, the prevent invention was accomplished. More specifically, the gist of the present invention is as follows.

(1) A hydrogel having a laminate structure of layer A and layer B, wherein
layer A
comprises a monomer-derived component, water, a humectant, a water-insoluble polymer having tackiness and an amphiphilic polymer,
the water-insoluble polymer is comprised in a proportion of 3 to 20 wt % based on a total amount of layer A, and
the amphiphilic polymer is a polyvinyl alcohol having a saponification degree of 50 to 75% and is comprised in a proportion of 0.05 to 5 wt % based on the total amount of layer A;
layer B
comprises a monomer-derived component, water and a humectant and
is substantially free of a water-insoluble polymer having tackiness and a polyvinyl alcohol;
an amount of the water based on a total amount of layer B is the amount of water based on the total amount of layer A±10 wt %; and an amount of the humectant based on the total amount of layer B is an amount of the humectant based on the total amount of layer A±10 wt %.
(2) The hydrogel according to (1), wherein the monomer-derived component in layer A and the monomer-derived component in Layer B are identical as a compound.
(3) The hydrogel according to (1) or (2), wherein the humectant is a polyhydric alcohol.
(4) The hydrogel according to any one of (1) to (3), wherein adhesive forces of layer A and layer B to a Bakelite plate are 5 to 15 N/20 mm and 0.5 to 7 N/20 mm, respectively.
(5) The hydrogel according to any one of (1) to (4), wherein an intermediate substrate is embedded in the hydrogel having a laminate structure along an in-plane direction.
(6) The hydrogel according to (5), wherein the intermediate substrate is a semipermeable membrane.
(7) A medical-electrode hydrogel to be placed between an electrode constituted of a conductive material and a skin surface when in use, and consisting of the hydrogel according to any one of (1) to (6), wherein layer A is a layer in contact with the electrode and layer B is a layer in contact with the skin surface.

The specification includes the contents disclosed in JP Patent Application Nos. 2016-193679 and 2017-031855, based on which the present application claims.

Advantageous Effects of Invention

According to the present invention, it is possible to obtain a hydrogel having a low moisture absorption rate on the side facing an electrode element, i.e., having a low reduction rate of adhesive force under a high-humidity environment, and keeping an optimal adhesive force on the side facing the skin. The hydrogel is suitably used as a medical-electrode hydrogel for use in adhering to the skin.

BRIEF DESCRIPTION OF DRAWING

FIG. 1 is a schematic sectional view of a hydrogel according to an embodiment of the present invention.

DESCRIPTION OF THE EMBODIMENTS

Now, the present invention will be more specifically described below.

FIG. 1 shows a sectional view of a hydrogel according to an embodiment of the present invention. A hydrogel 1 according to the embodiment is constituted by laminating layer A 10 and layer B 20. Next, individual compositions of layer A 10 and layer B 20 will be described.

Layer A 10 contains a monomer-derived component, water, a humectant, a water-insoluble polymer having tackiness and an amphiphilic polymer. It is characterized in that the water-insoluble polymer is contained in a proportion of 3 to 20 wt % based on the total amount of layer A; and that the amphiphilic polymer is a polyvinyl alcohol having a saponification degree of 50 to 75% and is contained in a proportion of 0.05 to 5 wt % based on the total amount of layer A.

(Monomer-Derived Component)

The monomer-derived component to be used in layer A is contained as a water-soluble polymer having a cross-linkage due to polymerization. The water-soluble polymer can be obtained by copolymerization of a non-crosslinkable monomer and a crosslinkable monomer. For example, a copolymer of a water-soluble (meth)acrylic monomer and a crosslinkable monomer having two or more alkenyl groups, can be used.

Examples of the (meth)acrylic monomer may include a (meth)acrylamide, a N-alkyl modified (meth)acrylamide, a N,N-dialkyl modified (meth)acrylamide, (meth)acrylic acid and an alkyl (meth)acrylate. Also, a water-soluble monomer such as N-vinyl amide is mentioned as an example.

Examples of the crosslinkable monomer having two or more alkenyl groups include a multifunctional acrylate and a multifunctional acrylamide.

Owing to the crosslinked water-soluble polymer, the matrix of the water-soluble polymer can be constituted. More specifically, a hydrogel having a composition containing a crosslinked water-soluble polymer constituted of a monomer-derived component, water, a humectant and an amphiphilic polymer, and constituted of a matrix of the water-soluble polymer containing water, the humectant and the amphiphilic polymer can be obtained.

Specific examples of the non-crosslinkable monomer constituting a water-soluble polymer serving as a monomer-derived component include non-electrolyte based acrylamide derivatives such as (meth)acrylamide, N-methyl(meth)acrylamide, N-ethyl(meth)acrylamide, N-propyl(meth)acrylamide, N,N-dimethyl(meth)acrylamide, N,N-diethyl(meth)acrylamide and acryloylmorpholine; electrolyte based acrylamide derivatives such as tertiary butylacrylamide sulfonic acid (TBAS) and/or a salt thereof, a N,N-dimethylaminoethyacrylamide (DMAEAA) hydrochloride and a N,N-dimethylaminopropylactylamide (DMAPAA) hydrochloride; electrolytic acrylic derivatives such as (meth)acrylic acid, maleic acid, itaconic acid, sulfopropyl methacrylate (SPM) and/or a salt thereof and methacryloyloxyethyltrimethylammonium chloride (QDM); and non-electrolyte based acrylic derivatives such as hydroxyethyl (meth)acrylate and polyethylene glycol (meth)acrylate.

Examples of the crosslinkable monomer include N,N'-methylenebis(meth)acrylamide, ethylene glycol di(meth)acrylate, polyethylene glycol di(meth)acrylate and glycerin tri(meth)acrylate.

The content of the crosslinked water-soluble polymer in layer A is not particularly limited as long as, in a liquid composition prepared by adding a non-crosslinkable monomer and a crosslinkable monomer, the non-crosslinkable monomer and the crosslinkable monomer are homogeneously dissolved. However, the crosslinked water-soluble polymer is preferably contained in a proportion of 15 wt % or more based on the total amount of layer A in order to maintain gel strength of the resultant gel form and improve shape retention and processability, and further preferably contained in a proportion of 18 wt % or more.

To form a matrix of the crosslinked water-soluble polymer, a non-crosslinkable monomer is used. As the non-crosslinkable monomer, a monomer basically soluble in water and having a high solubility to water is preferable. Particularly, if a monomer present in a liquid state at normal temperature is used, a monomer dissolved in water in any ratio is preferable. In contrast, in the composition constituting layer A, other than water and a monomer, additives such as a humectant, optionally an electrolyte salt and a polymerization initiator sometimes need to be dissolved. In the cases, the concentration of the crosslinked water-soluble polymer based on the total amount of layer A is preferably set to be 35 wt % or less and further preferably 30 wt % or less.

The content of the crosslinkable monomer relative the total amount of layer A should be appropriately set depending on the molecular weight and chemical and physical properties of the non-crosslinkable monomer mentioned above or the crosslinkable monomer. In order to improve shape retention of the gel form to be obtained, the content is preferably set to be 0.01 wt % or more and further preferably 0.05 wt % or more. Conversely, the gel form preferably has flexibility as long as shape retention is not impaired, because initial tack can be easily obtained when it is used as an adhesive. Because of this, the content is preferably set to be 1.0 wt % or less and further preferably 0.6 wt % or less.

As described above, since the non-crosslinkable monomer occupies a large portion of the matrix, the non-crosslinkable monomer preferably has a high water solubility. The solubility is, for example, preferably at least 20 (g/100 mL-$H_2O$) or more, further preferably 50 (g/100 mL-$H_2O$) or more, and most preferably 65 (g/100 mL-$H_2O$) or more.

Since the crosslinkable monomer partly constitutes the matrix, even if the crosslinkable monomer to be used is not soluble in water, the hydrophilicity of the whole matrix will not be damaged. As a method for dissolving a crosslinkable monomer low in solubility to water in the liquid composition, if the crosslinkable monomer is liquid, a method of dissolving the crosslinkable monomer in a non-crosslinkable monomer is employed; or a method of dissolving the crosslinkable monomer not in a non-crosslinkable monomer but in a polyhydric alcohol serving as a humectant may be employed.

(Humectant)

To improve moisture-retaining property and plasticity, a humectant is added to layer A. As the humectant, a polyhydric alcohol is preferably used. Examples of the polyhydric alcohol that can be used include diols such as ethylene glycol, propylene glycol and butanediol; polyhydric alcohols such as glycerin, pentaerythritol and sorbitol; polyhydric alcohol condensates such as polyethylene glycol, polypropylene glycol and polyglycerin; and modified polyhydric alcohols such as polyoxyethylene glycerin. Note that, as the humectant, it is preferable to use a polyhydric alcohol present in a state of liquid at normal temperature (preferably a temperature of 10° C. below zero or more), more specifically, in the temperature range where a gel form is actually used (for example, around 20° C. when used indoors).

Since water is contained in layer A, water is vaporized in a short time and/or layer A is easily dried without a humectant. Further plasticity is damaged, and tackiness, particularly, initial tack force, tends to significantly reduce. When the hydrogel of the present invention is employed in uses requiring conductivity such as a medical electrode, if water is vaporized, the impedance of the electrode increases, and if the impedance of the electrode exceeds a predetermined value, the electrode cannot be used. Accordingly, the humectant is added to layer A to prevent vaporization of water in a predetermined amount or more. Furthermore, if the humectant is liquid at normal temperature, the humectant itself serves also as a plasticizer.

The concentration of a humectant in layer A is preferably 35 wt % or more based on the total amount of layer A and more preferably 40 wt % or more in order to maintain moisture-retaining property and plasticity and exhibit excellent stability. The amount of the humectant is preferably 70 wt % or less based on the total amount of layer A and more preferably 65 wt % or less, in order to keep a predetermined solid content of a resin for the purpose of ensuring elastic strength and the adhesive force of the gel form to be obtained.

(Water)

The concentration of water contained in layer A is preferably 13 wt % or more in a liquid composition in order to stably disperse a water-insoluble polymer having tackiness, more specifically, the concentration is preferably 13 wt % or more based on the total amount of layer A and further preferably 18 wt % or more. In order to suppress variation of gel properties caused by vaporization and dryness and stabilize the gel properties, the concentration of water based on the total amount of layer A is preferably set to be 40 wt % or less and further preferably 30 wt % or less. For example, if glycerin is used as a humectant, glycerin has a property (moisture-retaining property) of maintaining about 20 to about 40 wt % of moisture relative to its own weight in the range of a relative humidity of about 50% to 70%. The inventors prepared hydrogels different in humectant and determined the moisture-retaining properties thereof at a relative humidity of 60%. As a result, the moisture-retaining property in the case of using, e.g., glycerin, was about 30 wt %, and the moisture-retaining property in the case of using sodium lactate was about 80 wt %.

As mentioned above, the moisture-retaining property of a humectant varies depending on the relative humidity and the moisture-retaining property of a hydrogel using (containing) a humectant varies similarly depending on the relative humidity. It is possible to control the moisture-retaining property of a gel at a predetermined humidity by using humectants different in moisture-retaining property in combination; however, the dependence of the moisture-retaining property of gel upon the relative humidity cannot be virtually controlled because the property is a nature intrinsic to a humectant. From the above, it is ideal that a humectant having a low moisture-retaining property (further ideally, a humectant is liquid at normal temperature) is used in a high concentration, and that apparent dependence of the moisture-retaining property of a gel upon the relative humidity can be lowered by controlling the moisture content to be low in designing the gel; however, it is preferable that layer A contains water in an amount satisfying the aforementioned concentration or more in order to stably disperse a water-insoluble polymer having tackiness.

(Water-Insoluble Polymer)

Examples of the water-insoluble polymer having tackiness include a polymer obtained by polymerizing hydrophobic monomers such as a (meth)acryl ester, vinyl acetate and a maleic ester, alone or in combination; more specifically, a homopolymer or co-polymer of hydrophobic monomers such as isooctyl (meth)acrylate, 2-ethylhexyl (meth)acrylate, butyl (meth)acrylate, vinyl acetate and dioctyl maleate. In addition to the aforementioned polymers, any one or more of hydrophobic monomers such as ethylene, propylene, butylene, methyl (meth)acrylate and ethyl (meth)acrylate may be copolymerized. Also, a silicone adhesive, a natural rubber adhesive and a synthetic rubber adhesive can be used. Of these, an acrylic ester copolymer is suitably used since it has been improved and is highly adhesive.

In order to disperse a water-insoluble polymer having tackiness in layer A, an emulsion prepared by dispersing/emulsifying a polymer as mentioned above is preferably used. The solid content of the emulsion is usually 30 to 60 wt % and the rest of the content is mostly water.

Examples of the emulsion of an acrylic ester copolymer resin suitably used include "Polysol PSA SE-1730" (trade name) manufactured by Showa Kobunshi K. K. and "VINYBLAN ADH-1048" (trade name) of Nissin Chemical Co., Ltd.

The content of the water-insoluble polymer having tackiness in layer A can be controlled in consideration of the effect of a final product to be expected. In order to obtain satisfactory adhesive force to an electrode element, the water-insoluble polymer having tackiness needs to be added in a proportion of 3 wt % or more based on the total amount of layer A, preferably 5 wt % or more, more preferably 8 wt % or more, and particularly preferably 10 wt % or more. Since the polymer has a function as an adhesive even if used alone, the polymer may be added in a large amount; however, if the amount added is excessive, the adhesive force will not increase over a certain value; and if the polymer is used as a medical-electrode hydrogel, conductivity of the gel decreases. In consideration of balance between these, the content of the water-insoluble polymer based on the total amount of layer A is set to be 20 wt % or less, preferably 15 wt % or less and more preferably 13 wt % or less.

The water-insoluble polymer having tackiness is preferably a copolymer hydrophobic monomer and a hydrophilic monomer as mentioned above. Copolymerization of a hydrophilic monomer with a hydrophobic monomer provides advantages that dispersion stability of the resultant polymer insoluble in water increases and the amounts of e.g., dispersant and a surfactant can be reduced.

If a water-insoluble polymer having tackiness is a copolymer constituted of a hydrophobic monomer and a hydrophilic monomer and having a copolymerization ratio of the hydrophilic monomer in the copolymer of 0.1 wt % or more, a dispersion stabilizing effect can be exerted. If the copolymerization ratio is more than 5 wt %, it becomes difficult to produce a polymer as mentioned above, as is described in JP Patent Publication (Kokai) No. 2002-80809A, JP Patent Publication (Kokai) No. 2003-336024A, and JP Patent Publication (Kokai) No. 2003-335805A. Accordingly, it is preferable to use a copolymer of a hydrophobic monomer and a hydrophilic monomer having a copolymerization ratio of the hydrophilic monomer of 0.1 to 5 wt % as the water-insoluble polymer.

Examples of the hydrophilic monomer include water-soluble monomers such as hydroxyethyl (meth)acrylate, polyethylene glycol (meth)acrylate, (meth)acrylamide, N-methyl(meth)acrylamide, N-ethyl(meth)acrylamide, N-propyl(meth)acrylamide, N,N-dimethyl(meth)acrylamide, N,N-diethyl(meth)acrylamide, acryloylmorpholine, tertiary butylacrylamide sulfonic acid (TBAS) and/or a salt thereof, N,N-dimethylaminoethylacrylamide (DMAEAA) hydrochloride, N,N-dimethylaminopropylacrylamide (DMAPAA) hydrochloride, (meth)acrylic acid, maleic acid, itaconic acid, sulfopropyl, methacrylate (SPM) and/or a salt thereof and methacryloyloxyethyltrimethylammonium chloride (QDM). Of these, a water-soluble monomer containing at least one carboxyl group is desirably contained, particularly, a (meth)acrylic acid and/or a salt thereof, which an ordinary monomer, can be suitably used. Of them, alkyl acrylate is preferably used.

(Amphiphilic Polymer)

Layer A of a hydrogel according to the embodiment contains an amphiphilic copolymer. Because of this, a satisfactory adhesive property to an electrode constituted of a conductive material can be obtained. In addition, since an amphiphilic polymer and a water-insoluble polymer having tackiness are contained, dispersion stability of the water-insoluble polymer becomes satisfactory. Particularly, in preparing a liquid composition for forming layer A, the dispersion stability of the water-insoluble polymer becomes satisfactory. Because of this, layer A of a hydrogel having more homogeneity and high quality stability can be satisfactorily obtained.

In the present invention, "amphiphilic" refers to being soluble at least in a solvent mixture of an organic solvent and water, preferably, soluble in both water and a polar organic solvent. Examples of solvent mixture of an organic solvent and water include a solvent mixture of ethanol/water=60/40. Accordingly, as the amphiphilic polymer, a polymer dissolved in a solvent mixture of ethanol/water=60/40 at room temperature is mentioned.

In the embodiment, as the amphiphilic polymer, a polyvinyl alcohol having a saponification degree of 50 to 75% is used. If the saponification degree is less than 50%, it is not impossible but difficult that the amphiphilic polymer is dissolved in water and handling of the polymer during production becomes worse. In contrast, if the saponification degree exceeds 75%, the solubility in water increases but salting out tends to increase. Such an amphiphilic polymer may not be suitable to the case where a large amount of an ionic additive such as an electrolyte is used. Note that, with respect to the saponification degree of a polyvinyl alcohol, a saponification degree of 98% or more is called as perfect saponification, a saponification degree of about 98% to 80% as a partial saponification, a saponification degree of 80% or less as low saponification. If the partial saponification is more specifically distinguished, a saponification degree of around 95% is called as intermediate saponification and a saponification degree of about 95% to 80% as partial saponification, as the case may be. The degree of saponification refers to a percentage calculated in accordance with the following equation:

$$\text{Saponification degree} = \text{polyvinyl alcohol unit}/(\text{vinyl acetate unit} + \text{polyvinyl alcohol unit}) \times 100$$

*calculation is made by substituting the amounts of substances (numbers of moles) of individual units into the equation.

Specific examples of the polyvinyl alcohol having a saponification degree of 50 to 75% include "J-POVAL JMR-10M" (trade name of Japan Vam & Poval CO., Ltd., a saponification degree: 65%); GOHSEFIMER LW-300" (trade name of Nippon Synthetic Chemical Industry Co.; saponification degree 53 to 60%), and "DENKA POVAL MP-10" (trade name of Denki Kagaku Kogyo K. K.; saponification degree 70%).

It is required that the amount of the amphiphilic polymer in layer A is 0.05 wt % or more based on the total amount of layer A in order to obtain a dispersion stability-enhancing effect of the liquid composition, and preferably 0.1 wt % or more. If the amount added is excessive, the viscosity of the liquid composition rises and it takes time to remove bubbles mixed during preparation of the liquid composition. If a large amount of an electrolyte is added, the water-insoluble polymer tends to be aggregated. Accordingly, the amount of the amphiphilic polymer based on the total amount of layer A is 5.0 wt % or less and preferably 4.0 wt % or less. The dispersion stability-enhancing effect can be sufficiently obtained by the amount added in the above range.

(pH Adjuster)

Layer A can be obtained by subjecting a liquid composition containing at least a monomer-derived component, water, a humectant, a water-insoluble polymer having tackiness, an amphiphilic polymer and a polymerization initiator to a polymerization reaction by heating or light irradiation. A water-soluble polymer matrix having a cross-linkage is formed by the polymerization reaction to obtain layer A. To layer A, a pH adjuster can be optionally added. The pH of the liquid composition is controlled to fall within the range of 4 to 7 by the pH adjuster, and then, the liquid composition is heated or exposed to light to carry out a polymerization reaction to obtain layer A.

If a water soluble acrylic ester and acrylamide derivative, even though they are a monomer or a polymer, are stored in an alkaline aqueous solution, hydrolysis of an ester group and an amide group basically proceeds. Conversely, hydrolysis also proceeds when pH is too acidic. Accordingly, it is possible to suppress hydrolysis of an acrylic monomer by controlling pH to fall within the range of 4 to 7, with the result that storage stability of a liquid composition and long-term storage stability after a gel is formed are improved.

The pH of the liquid composition can be controlled to fall within the range of 4 to 7 by adding a predetermined amount of a mineral acid and an organic acid as a pH adjuster. In this case, a multifunctional mineral acid and/or organic acid are preferably used. Furthermore, a mixture of an acid and a salt thereof is preferably used because a pH buffering action is exerted to stabilize pH.

Examples of the mineral acid include sulfuric acid, phosphoric acid and carbonic acid. Examples of the organic acid include multifunctional carboxylic acids such as citric acid, oxalic acid, malonic acid, succinic acid and tartaric acid. The amount of the mineral acid, the organic acid and these salts serving as a pH adjuster added to a liquid composition are not particularly limited and appropriately determined depending on the ability of the pH adjuster.

(Polymerization Initiator)

The liquid composition usually contains a photopolymerization initiator.

As the photopolymerization initiator, a compound generating a radical when it is cleaved by ultraviolet rays or visible light is suitably used. Examples thereof include α-hydroxy ketone, α-amino ketone, benzyl methyl ketal, bisacylphosphine oxide and metallocene. Specific examples thereof include 2-hydroxy-2-methyl-1-phenyl-propan-1-one (product name: DAROCUR 1173, manufactured by Ciba Specialty Chemicals), 1-hydroxy-cyclohexyl-phenyl-ketone (product name: IRGACURE 184, manufactured by Ciba Specialty Chemicals), 1-[4-(2-hydroxyethoxy)-phenyl]-2-hydroxy-2-methyl-propan-1-one (product name: IRGACURE 2959, manufactured by Ciba Specialty Chemicals), 2-methyl-1-[(methylthio)phenyl]-2-morpholinopropan-1-one (product name: IRGACURE 907, manufactured by Ciba Specialty Chemicals), 2-benzyl-2-dimethylamino-1-(4-morpholinophenyl)-butan-1-one (product name: IRGACURE 369, manufactured by Ciba Specialty Chemicals), 2-hydroxy-1-{4-[4-(2-hydroxy-2-methyl-propionyl)-benzyl]phenyl}-2-methyl-propan-1-one (product name: IRGACURE 127, manufactured by Ciba Specialty Chemicals). These can be used alone or in combination.

In order to sufficiently carry out a polymerization reaction and reduce the residual amount of a monomer, the amount of the photopolymerization initiator added is preferably 0.01 wt % or more based on the liquid composition (100 wt %) before gelatinization; and in order to prevent discoloration (yellowing) and odor caused by an unreacted photopolymerization initiator, the amount thereof added is preferably 1.0 wt % or less and more preferably 0.05 to 0.5 wt %.

(Electrolyte)

If the hydrogel of the present invention is used in electrodes such as a biopotential measurement electrode for use in cardiac electrogram (ECG), electroencephalogram, nystagmus and myoelectricity, an electrostimulation electrode for use in TENS and low frequency treatment; an electroscalpel counter-electrode; and an electrode for iontophoresis, conductivity can be improved by adding an electrolyte salt. As the electrolyte salt, a chloride of an alkali metal or an alkaline earth metal is preferable.

Preferable examples of the electrolyte salt include chlorides of lithium, sodium, potassium, magnesium and calcium. These may be used alone or in combination.

If an electrolyte salt is added in order to provide conductivity, the amount of the electrolyte salt added is preferably at least 0.5 wt % or more based on the total amount of layer A. If an electrolyte is added in a large amount, conductivity is improved; however, if the electrolyte salt is excessively added, aggregation tendency of a water-insoluble polymer increases. Furthermore, if the amount added exceeds a predetermined amount, merits such as conductivity improvement are overwhelmed by demerits such as aggregation and elongation of dissolution time during a liquid composition preparation process. Thus, the amount added is preferably 6.0 wt % or less based on the total amount of layer A, and more preferably 4.0 wt % or less.

(Surfactant)

To the liquid composition for forming layer A, a surfactant can be added. Owing to the surfactant, tendency to aggregation of a water-insoluble polymer and an amphiphilic polymer due to salting out can be reduced. Particularly, a surfactant having a polyoxyethylene alkyl ether sulfate group is preferable. Preferable examples of the surfactant include compounds having structures represented by (Formula 1) to (Formula 6).

[Formula 1]

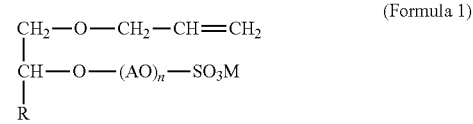

(Formula 1)

[Formula 2]

(Formula 2)

[Formula 3]

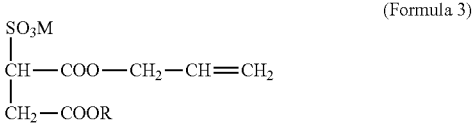

(Formula 3)

[Formula 4]

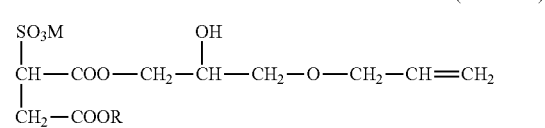

(Formula 4)

[Formula 5]

(Formula 5)

[Formula 6]

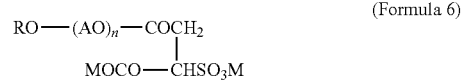

(Formula 6)

In the above formulas, R represents an alkyl group; M an ammonium salt or an alkali metal salt; AO an alkylene oxide (ethylene oxide or propylene oxide); and n an integer of 1 to 50.

Examples of a compound having a structure represented by (Formula 1) include Aqualon KH-05, KH-10 (manufactured by Dai-ichi Kogyo Seiyaku Co., Ltd.). Examples of a compound having a structure represented by (Formula 2) include Eleminol RS-30 (manufactured by Sanyo Chemical Industries Ltd.). Examples of a compound having a structure represented by (Formula 3) include Eleminol JS-2 (manufactured by Sanyo Chemical Industries Ltd.). Examples of a compound having a structure represented by (Formula 4) include LATEMUL S-180A, S-180 (manufactured by Kao Corp.). Examples of a compound having a structure represented by (Formula 5) include EMAL D-3-D, LATEMUL-118B, E-150, LEVENOL WX (manufactured by Kao Corp.), HITENOL 08E, 18E, LA series (manufactured by Dai-ichi Kogyo Seiyaku Co., Ltd.). Examples of a compound having a structure represented by (Formula 6) include Newcol 293, RA544 (manufactured by Nippon Nyukazai Co., Ltd.).

In order to obtain an effect of the surfactant to be added, the surfactant is preferably added in a proportion of 0.1 wt % or more relative to the liquid composition. In consideration of the effect on tackiness and other properties, an amount added of 2.0 wt % or less relative to the liquid composition is preferable. A method for adding a surfactant is not particularly limited.

(Peroxide)

At least 0.003 wt % of a peroxide may be optionally added to the liquid composition to successfully prevent yellow discoloration of a gel after polymerization. Note that, even if 0.3 wt % or more of a peroxide is added to the liquid composition, yellowing discoloration-preventing effect does not significantly change. Besides this, the peroxide remains in a large amount in the gel and increases a risk of eroding a conductive material constituting an electrode when the gel is used, for example, in a medical electrode. The peroxide remaining in the gel decreases by aging the gel for a certain period after the formation thereof. The term "aging" refers to a process where a gel is allowed to stand still in a predetermined temperature condition to accelerate decomposition of e.g., a peroxide. To accelerate decomposition of a peroxide, the aging temperature is preferably set to be 30° C. or more. If the aging temperature is excessively high, there is a risk of decomposition/deterioration of a gel matrix. Furthermore, a protective film attached to the gel shrinks, producing a risk of generating wrinkle and deformation. Because of this, the aging temperature is preferably set to be 60° C. or less. The aging temperature is most preferably 35 to 45° C.

Examples of the peroxide include hydrogen peroxide, sodium percarbonate, sodium perborate, peracetic acid and chlorine dioxide. These peroxides are preferably diluted with water up to a concentration of 10% or less, and then, added to the liquid composition. Once a peroxide is added to the liquid composition, the liquid composition must be used within 24 hours. If the liquid composition is allowed to stand still for a long time after a peroxide is added, a polymerization reaction is initiated and a gel may possibly generate at unintended timing.

Next, the composition of layer B 20 to be laminated on layer A 10 will be described. Layer B 20 is characterized in that it contains a monomer-derived component, water and a humectant, and is substantially free of a water-insoluble polymer having tackiness and a polyvinyl alcohol serving as an amphiphilic polymer, which are added to layer A. Since neither a water-insoluble polymer nor a polyvinyl alcohol is added, the tackiness of layer B is low and an optimal adhesive force to the skin surface is obtained and no skin damage occurs.

The types and amounts of the monomer-derived component, water and humectant in layer B are the same as in layer A. The amount of water based on the total amount of layer B is the amount of water based on the total amount of layer A±10 wt %. The amount of the humectant based on the total amount of layer B is set to fall within the range of the amount of the humectant based on the total amount of layer A±10 wt %. If the amount falls within this range, the adhesion properties of layer A and layer B are satisfactory. Even if the gel is used as a hydrogel of a medical electrode, the hydrogel is preferentially removed from the skin surface without removal between layer A and layer B. Note that, water and a humectant slightly migrate from layer A to layer B (or vice versa) with time after production of hydrogel 1; however, if the contents of water and the humectant fall within the range of ±10 wt % in the gel which reaches a steady state via the migration, the gel falls within the scope of the present invention.

In the hydrogel according to the embodiment, the contents of water to be contained in layer A and layer B, which are not limited, can be determined by a method comprising the steps of taking out a sample of layer A or layer B having a predetermined weight, drying the sample, measuring the dry weight thereof and calculating a difference between the initial weight and the dry weight; or determined by a volumetric titration method or coulometric titration method using, e.g., a Karl Fischer moisture measuring device.

In the hydrogel according to the embodiment, the contents of a humectant to be contained in layer A and layer B, which are not limited, can be measured by a method such as a solvent extraction method or a means such as liquid chromatography (LC).

The monomer-derived component in layer A and the monomer-derived component in layer B may be different or the same compounds and preferably the same compounds. If the same compounds are used, the compositions for layer A and layer B become similar and the adhesion property between layers can be further improved.

Layer B of the hydrogel according to the embodiment may optionally contain a water-soluble polymer such as a polyacrylic acid or a salt thereof, in order to obtain an optimal adhesive force.

Examples of such a water-soluble polymer may include a copolymer of an acrylic acid and a methacrylic acid and a polymer containing N-alkyl sulfonic acid acrylamide as a structural unit. These may be used alone or in combination.

The copolymer of acrylic acid and methacrylic acid preferably has a copolymerization ratio (molar ratio) of the acrylic acid and the methacrylic acid of 9:1 to 1:9.

If the content of a copolymer of an acrylic acid and methacrylic acid is excessively low, it is difficult to obtain a desired adhesive force. Conversely, if the content is excessively large, the hydrogel becomes hard, with the result that adhesive force becomes low. The content is appropriately determined in consideration of balance between these. More specifically, the content of the copolymer based on the total amount of layer B is preferably 0.03 to 3 wt % and more preferably 0.2 to 2 wt %.

The copolymer of acrylic acid and methacrylic acid can be produced by a method such as radical polymerization, a redox reaction and light irradiation. Examples of the copolymer of acrylic acid and methacrylic acid that can be used may include commercially available products such as JURYMER AC-20H, AC-20L, (trade name) manufactured by Toagosei Co., Ltd., and FL-200 (trade name) manufactured by NIPPON SHOKUBAI CO., LTD.

The weight average molecular weight of a polymer containing N-alkyl sulfonic acid acrylamide as a structural unit, which is not particularly limited, is preferably 7,000,000 or less in order to easily prepare a liquid composition and produce optimal adhesive force by the resultant hydrogel, and also preferably 500,000 or more in order to obtain a gel having aggregability.

The content of a polymer containing N-alkyl sulfonic acid acrylamide as a structural unit based on the total amount of layer B is preferably 0.1 to 40 wt % and more preferably 0.4 to 15 wt %.

The polymer containing N-alkyl sulfonic acid acrylamide as a structural unit may be a copolymer with another polymer. As a commercially available copolymer as mentioned above, a copolymer of acrylic acid and N-alkyl sulfonic acid acrylamide may be mentioned. Specific examples thereof that can be used include a copolymer of acrylic acid and acrylamido-methylpropane sulfonic acid (Aron-bis AH-305 (trade name) manufactured by Toagosei Co., Ltd.).

If the polymer containing N-alkyl sulfonic acid acrylamide as a structural unit is a copolymer with another polymer, the copolymerization ratio (molar ratio) of N-alkyl sulfonic acid acrylamide-containing polymer to another polymer is preferably 2:8 to 8:2 and more preferably 2:8 to 5:5.

The components of layer B except a monomer-derived component, water, a humectant and a water-soluble polymer optionally added, i.e., optional components, such as a pH adjuster, an electrolyte, a surfactant and a peroxide are the same as in the case of layer A.

In hydrogel 1 of the embodiment, since layer A 10 contains a predetermined water-insoluble polymer and a polyvinyl alcohol serving as an amphiphilic polymer in predetermined amounts, initial tack is high and the moisture absorption rate is low, with the result that reduction in adhesive force under a high humidity environment is low. In contrast, layer B 20 has a smaller adhesive force than layer A and an excellent adhesion property to layer A. Taking advantage of the feature, the hydrogel 1 of the embodiment, which is allowed to adhere to an electrode 30 constituted of a conductive material such that the electrode 30 faces layer A 10, as shown in FIG. 1, can be used as a medical-electrode hydrogel. As shown in FIG. 1, on layer B 20, further a protective film 40, such as a polyethylene terephthalate film, treated with a mold-releasing agent, is laminated. The protective film 40 is removed prior to use, and then, layer B 20 is allowed to adhere to the skin. Since reduction in adhesive force of layer A 10 by sweat and moisture on the skin surface is low, the electrode element will not be removed.

The electrode 30 can be obtained by forming a conductive layer by print-coating of a resin film serving as a surface substrate 50 with a conductive ink containing, e.g., a metal such as Ag, Ag/AgCl and carbon or by lamination of a metal foil (e.g., aluminum, stainless steel, Ag) or a conductive film containing carbon on a resin film serving as the surface substrate 50.

The thickness of the resin film serving as the surface substrate 50 is satisfactorily about 5 μm to 150 μm. The material for the resin film, which is not particularly limited, is preferably, e.g., synthetic paper (polypropylene containing an inorganic filler) suitable for printing, a PET film and an OPP film. To improve appearance, on the surface of the surface substrate 50 opposite to the surface facing the electrode 30, decorative print may be made or paper, nonwoven fabric, foam (soft expanded-sheet made of, e.g., polyethylene, polyethylene vinyl acetate, polyurethane) or a film or sheet of, e.g., polyurethane may be laminated as long as flexibility is not damaged.

In consideration of use as a hydrogel for, e.g., a medical electrode, the adhesive forces of layer A and layer B, which are specified as adhesive forces to a Bakelite (phenol-formaldehyde resin) plate, preferably fall within the ranges of 5 to 15 N/20 mm and 0.5 to 7 N/20 mm, respectively. More preferably, the adhesive force of layer A is 7 to 12 N/20 mm; whereas, the adhesive force of layer B is 2 to 5 N/20 mm. If the adhesive forces fall within the ranges, the adhesive forces to electrode 30 and to skin surface are optimal. Note that, the adhesive force to a Bakelite plate herein is determined as follows: test pieces are prepared by cutting a hydrogel into pieces of 120 mm×20 mm in size; attaching a Bakelite plate to layer A-side or layer B-side of a measurement target; and pressing the plate by reciprocally moving a pressure roller (2 kg). Then, a stress value (N/20 mm) was measured by a rheometer (CR-500DX, manufactured by Sun Scientific Co., Ltd.) in accordance with JIS-Z0237:2009 in the measurement conditions: angle: 90° and speed: 300 mm/min at a measurement initiation point and predetermined peeling-off points (30, 40, 50, 60, 70 mm). The measurement is repeated three times and the values (total: 15 points) were averaged and determined as the adhesive force. The measurement is carried out under the environment: temperature: 23±5° C. and humidity: 55%±10%.

The thickness of each of layer A 10 and layer B 20 is appropriately set in consideration of use or the like. More specifically, the thickness of layer A is 0.2 to 1.2 mm and the thickness of layer B is 0.2 to 1.2 mm. The thickness ratio of layer A and layer B is preferably 1:6 to 6:1 and more preferably 1:3 to 3:1.

In the hydrogel 1, if necessary, nonwoven fabric or woven fabric can be embedded as an intermediate substrate along the in-plane direction of the hydrogel 1. The intermediate substrate is used for strengthening the gel and improving shape retention during a cutting process. For example, when the hydrogel 1 is distributed as an intermediate material for processing, the intermediate substrate is necessary for making handling easier for end-processers. As the material for nonwoven fabric and woven fabric, a natural fiber such as cellulose, silk and linen; a synthetic fiber such as polyester, nylon, rayon, polyethylene, polypropylene and polyurethane, or a blend of these can be used.

As the intermediate substrate, a semipermeable membrane can be suitably used. The semipermeable membrane is constituted of, e.g., cellophane or cellulose acetate. Since the semipermeable membrane hardly permits water and a humectant to pass compared to woven fabric or nonwoven fabric, the compositions of layer A and layer B immediately after production can be maintained for a longer time.

If the intermediate substrate is excessively thick, permeability of the substrate with a liquid decreases and sometimes a harmful effect is produced on conductivity. Conversely, if the intermediate substrate is excessively thin, e.g., successful strengthening of the hydrogel may not be made, similarly to the case where a basis weight is extremely small. In consideration of these, the thickness is appropriately set. The thickness preferably falls within the range of 0.02 to 2.0 mm, more preferably 0.02 to 0.5 mm and particularly preferably 0.03 to 0.3 mm.

The whole thickness of the hydrogel in the present invention is preferably 0.4 to 2.4 mm, more preferably 0.6 to 1.5 mm and particularly preferably 0.7 to 1.0 mm. Note that, the thickness of the hydrogel can be determined through measurement by, e.g., a micrometer.

The hydrogel 1 is produced by preparing liquid compositions containing requisite components respectively for layer A and layer B, subjecting these liquid compositions sequentially to polymerization by heating or light irradiation and laminating the polymerized materials.

In the case of the liquid composition for layer A, for example, an amphiphilic polymer previously dissolved in water is, if necessary, further diluted with water and homogeneously stirred to prepare a solution. To the solution, an emulsion of a water-insoluble polymer is added and homogeneously dispersed. Subsequently, a humectant is introduced and stirred until it is homogeneously dispersed. This is designated as [liquid 1].

To [liquid 1], a monomer is added and stirred. Depending on type of monomer, absorption or generation of heat sometimes occurs during dissolution. When absorption of heat occurs, it is preferable to warm up the liquid. When generation of heat occurs, it is preferable to cool the liquid. In warming up or cooling, the temperature of [liquid 1] is preferably controlled to fall within the range of 10° C. to 50° C. and more preferably 20° C. to 40° C. If the temperature is excessively low, a long time is required for dissolving the monomer itself; particularly, a solid monomer takes long time. Moreover, it takes a long time for dissolving additives other than the monomer. Depending on the type of component to be added, dissolution cannot be made if the temperature is excessively low. Furthermore, if the temperature extremely decreases, an emulsion is formed and other polymer components are sometimes aggregated. If the temperature is extremely high, dispersibility of an emulsion gets worse. If a highly reactive component is contained, a reaction is initiated or extremely accelerated, and, in other cases, volatile components in the liquid composition evaporate, with the result that a liquid composition cannot be obtained just as designed.

In the case where an electrolyte is required, the electrolyte is preferably added next to a monomer addition step. When an electrolyte is added, an emulsion is formed or other polymer components are sometimes aggregated by salting out; however, if the monomer is previously dissolved, the aggregation can be effectively suppressed. This is presumably because the monomer itself serves like a surfactant; however, a specific mechanism is unknown.

Next, requisite components other than those mentioned above and a polymerization initiator are added and stirred/mixed until all components are completely dissolved. In this manner, a liquid composition can be obtained.

The liquid composition for layer B can be prepared in the same manner as in the liquid composition for layer A except that neither a water-insoluble polymer nor a polyvinyl alcohol serving as an amphiphilic polymer are added. Note that, the procedures for preparing the liquid compositions of layer A and layer B are not limited to those mentioned above.

Storage conditions of individual liquid compositions are not particularly limited as long as the emulsion to be added and other components are kept stable. The liquid compositions are preferably stored in the range of 0° C. to 50° C. and further preferably in the range of 5° C. to 40° C.

A method for producing hydrogel 1, which varies depending on detailed conditions such as the compositions of layer A and layer B, the material for an intermediate substrate and the thickness thereof, is not particularly limited. For example, if an intermediate substrate is embedded, any one of the following methods can be appropriately employed: a method comprising the steps of suspending the intermediate substrate in the air while a predetermined tension or more is applied to the intermediate substrate; pouring a monomer liquid-composition into spaces on and under the intermediate substrate and polymerizing the monomer liquid composition with, e.g., light irradiation to obtain a sheet-like form; a method comprising the steps of preparing respective sheet-like gel materials of layer A and layer B having a smooth surface, sandwiching an intermediate substrate, which is suspended while applying a predetermined tension or more, by these gel materials to obtain a composite; and a method comprising the steps of preparing a sheet-like layer A having a smooth surface, optionally placing an intermediate substrate, to which a predetermined tension or more is applied, on layer A, pouring a monomer liquid composition for layer B into a space on the intermediate substrate; polymerizing the composition with, e.g. light irradiation. Herein, if a roll-form hydrogel is supplied, a production process as mentioned above can be continuously carried out.

Usually, a liquid composition for layer B is first added dropwise on, e.g., a resin film (base film). The liquid composition is spread by placing, e.g., a resin film (top film) treated with a mold-releasing agent over the upper surface of the base film, and controlled to have a predetermined thickness. In this state, heat or light (ultraviolet rays) is applied to polymerize (crosslink) the liquid composition to obtain a gel form having the predetermined thickness. As the base film, e.g., polyester, polyolefin, polystyrene or polyurethane, paper or paper laminated with a resin film can be used.

If the base film is used as the protective film 40, a film prepared by applying a mold-releasing agent to the surface of e.g., polyester, polyolefin or polystyrene, paper or paper laminated with a resin film, can be suitably used. Particularly, e.g., a biaxially stretched PET film and OPP are preferable. As the treatment method with a mold-releasing agent, silicon coating is mentioned; in particular, silicon coating by baking is preferable, in which a curing (cross-linking) reaction is carried out with application of heat or ultraviolet rays.

As the top film, the same material as used in the base film can be basically used. If a gel is formed by light irradiation, it is necessary to select a material that does not block light.

After the gel is continuously polymerized by formation of cross-linkage, an intermediate substrate is optionally placed on layer B produced. On layer B, a liquid composition for layer A is added dropwise and spread by further placing a top film in the same manner as in forming layer B. Heat or light is applied to polymerize (crosslink) the liquid composition. In this manner, a hydrogel constituted of a laminate structure of layer A and layer B can be obtained.

Each of the liquid compositions for layer A and layer B may contain a hydrophilic polymer serving as a tackifier as long as dispersibility of the emulsion is not worsened. For example, a polyacrylic acid and a salt thereof, a polyvinylpyrrolidone, a polyvinyl alcohol (not amphiphilic) and a polyethylene oxide can be used. As a tackifier for an emulsion, e.g., a rhodine based resin may be added.

To a liquid composition, e.g., an antiseptic agent, a germicidal agent, an antifungal agent, an antirust agent, an antioxidizing agent, a stabilizer, a flavor and a coloring agent; as well as an anti-inflammatory agent, a vitamin, a whitening agent and other medicinal ingredients may be optionally and appropriately added.

EXAMPLES

Now, the present invention will be more specifically described based on Examples and Comparative Examples; however, the present invention is not limited to these examples.

Example 1

Preparation for Liquid Composition for Layer A

Using a stirring/mixing container, acrylamide as a non-crosslinkable monomer, methylenebisacrylamide as a crosslinkable monomer (18.9 wt % in total) and ion exchange water (9.8 wt %) were mixed as shown in Table 1, stirred and homogeneously dissolved. Then, glycerin (46.1 wt %) serving as a humectant was added to the mixture and stirred in the same manner as above until a homogeneous state was obtained. Subsequently, sodium chloride (2.1 wt %) serving as an electrolyte and (other) additives such as citric acid, sodium benzoate, a photo-polymerization initiator and a surfactant (0.3 wt % in total) were added and stirred until they were completely dissolved. Finally, 22.6 wt % (solid content: 11.3 wt %, water: 11.3 wt % of an emulsion of an acrylate copolymer (solid content: 50 wt %, trade name: "Polysol PSA SE-1730", manufactured by SHOWA HIGH-POLYMER CO., LTD.) serving as a water-insoluble polymer, and a polyvinyl alcohol (0.2 wt %) having a saponification degree of 65% serving as an amphiphilic polymer, were added and stirred for several minutes until a homogeneous state was obtained. In this manner, a milk-white liquid composition was obtained. In Table 1 herein, numerical values are described in terms of pure contents. More specifically, in the case of a water-insoluble polymer a, a solid content (11.3 wt %) in the aforementioned emulsion is listed. In the case of water c, the sum (21.1 wt %) of ion exchange water (9.8 wt %) and water (11.3 wt %) in the above emulsion was listed. The same applies to other Examples and Comparative Examples.

Preparation of Liquid Composition for Layer B

Using a stirring/mixing container, acrylamide as a non-crosslinkable monomer, methylenebisacrylamide as a crosslinkable monomer (21.4 wt % in total) and ion exchange water (23.8 wt %) were mixed as shown in Table 1, stirred and homogeneously dissolved. Then, glycerin (52.1 wt %) serving as a humectant was added to the mixture and stirred in the same manner as above until a homogeneous state was obtained. Subsequently, sodium chloride (2.4 wt %) serving as an electrolyte and other additives such as citric acid, sodium benzoate, and a photo-polymerization initiator (0.3 wt % in total) were added and stirred until they were completely dissolved. Thereafter, the mixture was stirred for several minutes to obtain a transparent liquid composition.

Production of Hydrogel

The liquid composition for layer B obtained was added dropwise on a PET film coated with silicone and allowed to pass through a clearance of a predetermined size to uniformly spread the liquid and the liquid film was fixed so as to have a thickness of 0.5 mm. This film was irradiated with ultraviolet rays at an energy amount of 500 mJ/cm$^2$ by use of a metal halide lamp to obtain layer B having a thickness of 0.5 mm. On layer B obtained, an intermediate substrate (nylon mesh) was placed. On the resultant construct, the liquid composition for layer A was added dropwise, and then, a PET film coated with silicone was placed thereon to uniformly spread the liquid and the liquid film was fixed so as to have a thickness of 0.5 mm. This film was irradiated with infrared rays at an energy amount of 3,000 ml/cm$^2$ (3,500 mJ/cm$^2$ in total to layer B) by use of a metal halide lamp to obtain a hydrogel having a total thickness of 1.0 mm.

Example 2

A liquid composition for layer A was prepared in the same manner as in Example 1 except that the contents (wt %) of components (a to f and h) were changed as shown in Table 1. A liquid composition for layer B was prepared in the same manner as in Example 1 except that 0.7 wt % of JURYMER AC-20H (trade name, manufactured by Toagosei Co., Ltd.) was added as a water-soluble polymer. A hydrogel was produced in the same manner as in Example 1 from these liquid compositions.

Examples 3 to 10

Liquid compositions for layer A and layer B were prepared in the same manner as in Example 1 except that the contents (wt %) of components (a to f and h) were changed as shown in Table 1. Hydrogels were produced in the same manner as in Example 1 from these liquid compositions.

Example 11

A liquid composition for layer A was prepared in the same manner as in Example 1 except that the contents (wt %) of components (a to f and h) were changed as shown in Table 2. A liquid composition for layer B was prepared in the same manner as in Example 1 except that 1.2 wt % JURYMER AC-20H (trade name, manufactured by Toagosei. Co., Ltd.) and 0.5 wt % Aron-bis AH-305X (trade name, manufactured by Toagosei Co., Ltd.) in an amount of 1.7 wt % in total were added as the water-soluble polymer, and contents (wt %) of components (c to f and h) were changed as shown in Table 2. A hydrogel was produced in the same manner as in Example 1 from these liquid compositions.

Example 12

Liquid compositions for layer A and layer B were prepared in the same manner as in Example 1 except that the contents (wt %) of components (a to h) were changed as shown in Table 2. As a water-soluble polymer (component g), JURYMER AC-20H (trade name, manufactured by Toagosei Co., Ltd.) was added. A hydrogel was produced in the same manner as in Example 1 from these liquid compositions.

Comparative Example 1

A liquid composition for layer A was prepared in the same manner as in Example 1 except that no water-insoluble polymer was added and contents (wt %) of components (h to f and h) were changed as shown in Table 2. A liquid composition for layer B was prepared in the same manner as in Example 1 except that the contents (wt %) of components (c to f and h) were changed as shown in Table 2. A hydrogel was produced in the same manner as in Example 1 from these liquid compositions.

Comparative Example 2

Liquid compositions for layer A and layer B were prepared in the same manner as in Example 1 except that the contents (wt %) of components (a to f and h) were changed as shown in Table 2. A hydrogel was produced in the same manner as in Example 1 from these liquid compositions.

Comparative Example 3

A liquid composition for layer A was tried to prepare in the same manner as in Example 1 except that a polyvinyl alcohol serving as an amphiphilic polymer was not added and the amount of glycerin was set to be 46.3 wt %. However, since the water-insoluble polymer was aggregated, a gel was not produced.

Comparative Example 4

A liquid composition for layer A was tried to prepare in the same manner as in Example 1 except that the contents (wt %) of components (a to f and h) were changed as shown in Table 2. However, since the viscosity of the liquid composition was high, a gel was not produced.

Comparative Examples 5 to 7

Liquid compositions for layer A and layer B were prepared in the same manner as in Example 1 except that the contents (wt %) of components (a to f and h) were changed as shown in Table 2. A hydrogel was produced in the same manner as in Example 1 from these liquid compositions.

TABLE 1

|  |  |  | Example |  |  |  |  |  |  |  |  |  |
|---|---|---|---|---|---|---|---|---|---|---|---|---|
|  |  |  | 1 | 2 | 3 | 4 | 5 | 6 | 7 | 8 | 9 | 10 |
| Layer A | Water-insoluble polymer a | Polysol (emulsion) | 11.3 | 11.3 | 4.9 | 16.5 | 11.3 | 11.2 | 11.3 | 11.3 | 11.4 | 11.1 |
|  | Amphiphilic polymer b | Polyvinyl alcohol | 0.2 | 0.2 | 0.2 | 0.2 | 0.1 | 2.8 | 0.2 | 0.2 | 0.2 | 0.2 |
|  | Water c | Ion exchanged water | 21.1 | 21.2 | 21.8 | 20.3 | 21.1 | 20.8 | 17.8 | 23.0 | 21.3 | 20.6 |
|  | Humectant d | Polyhydric alcohol (glycerin) | 46.1 | 45.5 | 51.1 | 42.2 | 46.2 | 44.2 | 49.4 | 44.2 | 45.6 | 41.6 |
|  | Monomer-derived component e | Non-crosslinkable monomer + crosslinkable monomer | 18.9 | 18.9 | 19.5 | 18.4 | 18.9 | 18.6 | 18.9 | 18.9 | 19.1 | 24.1 |
|  | Electrolyte f | Sodium chloride | 2.1 | 2.1 | 2.2 | 2.1 | 2.1 | 2.1 | 2.1 | 2.1 | 2.1 | 2.1 |
|  | Others h | Other additives | 0.3 | 0.8 | 0.3 | 0.3 | 0.3 | 0.3 | 0.3 | 0.3 | 0.3 | 0.3 |
|  |  | Total | 100 | 100 | 100 | 100 | 100 | 100 | 100 | 100 | 100 | 100 |
| Layer B | Water c | Ion exchanged Water | 23.8 | 23.8 | 23.8 | 23.9 | 23.8 | 23.8 | 20.1 | 25.9 | 23.6 | 24.9 |
|  | Humectant d | Polyhydric alcohol (glycerin) | 52.1 | 51.0 | 52.1 | 52.0 | 52.1 | 52.1 | 55.8 | 50.0 | 50.5 | 50.0 |
|  | Monomer-derived component e | Non-crosslinkable monomer + crosslinkable monomer | 21.4 | 21.3 | 21.4 | 21.4 | 21.4 | 21.4 | 21.4 | 21.4 | 23.2 | 22.3 |
|  | Electrolyte f | Sodium chloride | 2.4 | 2.4 | 2.4 | 2.4 | 2.4 | 2.4 | 2.4 | 2.4 | 2.4 | 2.5 |
|  | Water-soluble polymer g | Polyacrylic acid, etc. | 0 | 0.7 | 0 | 0 | 0 | 0 | 0 | 0 | 0 | 0 |
|  | Others h | Other additives | 0.3 | 0.8 | 0.3 | 0.3 | 0.3 | 0.3 | 0.3 | 0.3 | 0.3 | 0.3 |
|  |  | Total | 100 | 100 | 100 | 100 | 100 | 100 | 100 | 100 | 100 | 100 |
| Difference from layer A | | Water | −2.7 | −2.6 | −2.0 | −3.6 | −2.7 | −3.0 | −2.3 | −2.9 | −2.3 | −4.3 |
|  |  | Glycerin | −6.0 | −5.5 | −1.0 | −9.8 | −5.9 | −7.9 | −6.4 | −5.8 | −4.9 | −8.4 |
|  |  | Monomer-derived component | −2.5 | −2.4 | −1.9 | −3.0 | −2.5 | −2.8 | −2.5 | −2.5 | −4.1 | 1.8 |

Numerical values in Table: wt %

TABLE 2

|  |  |  | Example |  | Comparative Example |  |  |  |  |  |  |
|---|---|---|---|---|---|---|---|---|---|---|---|
|  |  |  | 11 | 12 | 1 | 2 | 3 | 4 | 5 | 6 | 7 |
| Layer A | Water-insoluble polymer a | Polysol (emulsion) | 11.0 | 11.3 | 0 | 22.2 | 11.3 | 10.8 | 17.4 | 17.4 | 10.6 |
|  | Amphiphilic polymer b | Polyvinyl alcohol | 0.2 | 0.2 | 0.2 | 0.2 | 0 | 9.0 | 0.2 | 0.2 | 0.2 |
|  | Water c | Ion exchanged water | 23.6 | 25.8 | 22.4 | 19.9 | 21.1 | 20.2 | 19.4 | 35.5 | 19.7 |
|  | Humectant d | Polyhydric alcohol (glycerin) | 44.7 | 39.8 | 54.9 | 37.7 | 46.3 | 39.7 | 34.7 | 18.6 | 36.5 |
|  | Monomer-derived component e | Non-crosslinkable monomer + crosslinkable monomer | 18.3 | 18.9 | 20.0 | 17.8 | 18.9 | 18.1 | 26.1 | 26.1 | 30.8 |
|  | Electrolyte f | Sodium chloride | 1.9 | 3.7 | 2.2 | 2.0 | 2.1 | 2.0 | 2.0 | 2.0 | 2.0 |
|  | Others h | Other additives | 0.3 | 0.3 | 0.3 | 0.2 | 0.3 | 0.2 | 0.2 | 0.2 | 0.2 |
|  |  | Total | 100 | 100 | 100 | 100 | 100 | 100 | 100 | 100 | 100 |
| Layer B | Water c | Ion exchanged water | 26.6 | 29.2 | 22.3 | 25.7 | 23.8 | 25.2 | 26.5 | 48.3 | 26.0 |
|  | Humectant d | Polyhydric alcohol (glycerin) | 50.4 | 44.9 | 55.0 | 48.5 | 52.1 | 49.5 | 47.0 | 25.2 | 47.9 |
|  | Monomer-derived component e | Non-crosslinkable monomer + crosslinkable monomer | 18.6 | 20.2 | 20.1 | 22.9 | 21.4 | 22.5 | 23.6 | 23.6 | 23.2 |
|  | Electrolyte f | Sodium chloride | 2.1 | 4.0 | 2.3 | 2.6 | 2.4 | 2.5 | 2.6 | 2.6 | 2.6 |
|  | Water-soluble polymer g | Polyacrylic acid, etc. | 1.7 | 1.1 | 0 | 0 | 0 | 0 | 0 | 0 | 0 |
|  | Others h | Other additives | 0.6 | 0.6 | 0.3 | 0.3 | 0.3 | 0.3 | 0.3 | 0.3 | 0.3 |
|  |  | Total | 100 | 100 | 100 | 100 | 100 | 100 | 100 | 100 | 100 |
| Difference from layer A | | Water | −3.0 | −3.4 | 0.1 | −5.8 | −2.7 | −5.0 | −7.1 | −12.8 | −6.3 |
|  |  | Glycerin | −5.7 | −5.1 | −0.1 | −10.8 | −5.8 | −9.8 | −12.3 | −6.6 | −11.4 |
|  |  | Monomer-derived component | −0.3 | −1.3 | −0.1 | −5.1 | −2.5 | −4.4 | 2.5 | 2.5 | 7.6 |

Numerical values in Table: wt %

(Evaluation of Adhesive Force)

With respect to the hydrogels obtained in Examples 1 to 12 and Comparative Examples 1 to 2 and 5 to 7, the adhesive forces of each of layer A and layer B to a Bakelite plate, carbon and skin were measured. Evaluation methods for the adhesive forces are as follows. The measurement results are shown in Table 3 and Table 4.

Evaluation of Adhesive Force (Bakelite Plate)

A hydrogel was cut into pieces of 120 mm×20 mm in size. A PET film was removed. To the gel surface exposed, a Bakelite plate was attached. A pressure roller (2 kg) was reciprocally moved to prepare test pieces. Measurement was carried out by using a rheometer (CR-500DX manufactured by Sun Scientific Co., Ltd.) in accordance with JIS-Z0237:2009 in the measurement conditions: an angle: 90° and speed: 300 mm/min. A stress value (N/20 mm) was measured at a measurement initiation point and predetermined peeling off points (30, 40, 50, 60, 70 mm). The measurement was repeated three times and the values (total: 15 points) were averaged. The obtained value was specified as the adhesive force of layer A or layer B. The measurement was carried out under the environment of a temperature of 23±5° C. and a humidity of 55%±10%.

Evaluation of Adhesive Force (Carbon)

A hydrogel was cut into pieces of 120 mm×20 mm in size. A PET film was removed. To the gel surface exposed, a backing material (e.g., PE foaming material (thickness: 1 mm) was laminated on PET #36 having one of the surfaces printed by carbon ink) was attached, and then, a pressure roller (2 kg) was reciprocally moved to prepare test pieces. Measurement was carried out by using a rheometer (CR-500DX manufactured by Sun Scientific Co., Ltd.) in accordance with JIS-Z0237:2009 in the measurement conditions: an angle: 90° and speed: 300 mm/min. A stress value (N/20 mm) was measured at a measurement initiation point and predetermined peeling off points (30, 40, 50, 60, 70 mm). The measurement was repeated three times and the values (total: 15 points) were averaged. The obtained value was specified as the adhesive force of layer A to carbon. The hydrogel was allowed to stand still under a high humidity environment (35° C., 90%)) for 5 minutes, and thereafter, the adhesive force to carbon was measured in the same manner as above. The measurement was carried out under the environment of a temperature of 23±5° C. and a humidity of 55%±10%.

Evaluation of Adhesive Force (Skin)

A hydrogel was cut into pieces of 120 mm×20 mm in size. A PET film was removed. To the gel surface exposed, a synthetic paper sheet coated with an inorganic filler was attached to provide a handle at the time of measurement. In this manner, test pieces were prepared. Thereafter, five test subjects (male and female of 20 s to 50 s) were allowed to enter a measurement room of the conditions: temperature: 23±5° C., humidity: 55%±10%, 15 minutes before attachment. The above test piece was attached to a portion (having as little skin hair as possible) inside a forearm of each of the test subjects. The state was maintained for 30 minutes. Measurement was carried out by using a rheometer (CR-500DX manufactured by Sun Scientific Co., Ltd.) in the measurement conditions: an angle of 180° and a speed: 1,000 mm/min. A stress value (N/20 mm) was measured at a measurement initiation point and predetermined peeling off points (30, 40, 50, 60, 70 mm). The measurement was repeated twice and the values (total: 10 points) were averaged. The obtained value was specified as the adhesive force of layer B to the skin.

(Interlayer Separation)

With respect to the hydrogels obtained in Examples 1 to 12 and Comparative Examples 1 to 2 and 5 to 7, whether layer A and layer B were separated or not was evaluated when they were removed from a Bakelite plate. An evaluation method is as follows. First, a hydrogel was cut into pieces of 120 mm×20 mm in size. A PET film was removed. To the gel surface exposed, a synthetic paper sheet coated with an inorganic filler was attached to provide a handle at the time of measurement and then a pressure roller (2 kg) was reciprocally moved to adhere. Then, the PET film on the opposite side was removed and the test piece was attached to a Bakelite plate. Thereafter, a pressure roller (2 kg) was reciprocally moved to obtain test pieces. A peel-off test of the hydrogel from the Bakelite plate was carried out by using a rheometer (CR-500DX manufactured by Sun Scientific Co., Ltd.) in accordance with JIS-Z0237:2009 in the measurement conditions: angle: 90° and speed: 300 mm/min. At that time, whether the layers were separated or not was visually observed. The results are shown in Table 3 and Table 4. In Tables, G (Good) indicates no separation of layers, and F (Fair) indicates partial separation, and P (Poor) indicates separation of layers.

TABLE 3

| | | | Example | | | | | | | | | |
|---|---|---|---|---|---|---|---|---|---|---|---|---|
| Evaluation | | | 1 | 2 | 3 | 4 | 5 | 6 | 7 | 8 | 9 | 10 |
| Adhesive force [N/20 mm] | Layer A | Bakelite | 11 | 11 | 10 | 11 | 11 | 10 | 11.5 | 11 | 10.5 | 10 |
| | | Carbon | 12 | 12 | 11 | 11.5 | 11.5 | 11.5 | 12 | 12 | 12 | 11 |
| | Layer B | Bakelite | 3.0 | 2.7 | 3.2 | 2.5 | 2.2 | 2.6 | 3.1 | 2.5 | 2.1 | 2.3 |
| | | Skin | 1.2 | 1.4 | 1.3 | 1.1 | 1.3 | 1.1 | 1.4 | 1.1 | 1.1 | 1.2 |
| Adhesive force (carbon) after standstill in high humidity environment (35° C. 90 %) for 5 minutes | | | 9.2 | 8.8 | 7.9 | 8.4 | 9.5 | 8.9 | 9.1 | 8.7 | 8.7 | 8.0 |
| Layer separation | | | G | G | G | G | G | G | G | G | G | G |

TABLE 4

| | | | Example | | Comparative Example | | | | | | |
|---|---|---|---|---|---|---|---|---|---|---|---|
| Evaluation | | | 11 | 12 | 1 | 2 | 3 | 4 | 5 | 6 | 7 |
| Adhesive force [n/20 mm] | Layer A | Bakelite | 11 | 12 | 5.5 | — | Water-insoluble polymer molecules were aggregated | Viscosity of liquid composition was high, difficult to stir | 10 | 8.5 | 6.8 |
| | | Carbon | 13 | 12.5 | 6.0 | — | | | 11 | 9.5 | 7.2 |
| | Layer B | Bakelite | 3.2 | 3.5 | 2.6 | — | | | 1.8 | 1.9 | 2.1 |
| | | Skin | 1.5 | 1.4 | 1.3 | — | | | 0.9 | 0.7 | 1.0 |
| Adhesive force (cation) after standstill in high humidity environment (35° C., 90%) for 5 minutes | | | 8.9 | 9.6 | 2.9 | — | | | 7.4 | 8.2 | 4.9 |
| Layer separation | | | G | G | G | P | | | F | F | G |

As shown in Table 3 and Table 4, owing to the present invention, a hydrogel excellent in adhesiveness to an electrode element, less reduced in tackiness and adhesiveness to an electrode element and an object even if it absorbs water such as sweat and moisture and having an optimal adhesive force to the skin surface.

REFERENCE SIGNS LIST 1 hydrogel
10 layer A
20 layer B
30 electrode
40 protective film
50 surface substrate All publications, patents and patent applications cited in the specification are incorporated herein in their entirety by reference.

The invention claimed is:

1. A hydrogel having a laminate structure of layer A and layer B, wherein
layer A
comprises a monomer-derived component, water, a humectant, a water-insoluble polymer having tackiness and an amphiphilic polymer,
the water-insoluble polymer is comprised in a proportion of 3 to 20 wt %, and water is comprised in a proportion of 13 to 40 wt %, based on a total amount of the layer A, and
the amphiphilic polymer is a polyvinyl alcohol having a saponification degree of 50 to 75% and is comprised in a proportion of 0.05 to 5 wt % based on the total amount of the layer A;
layer B
comprises a monomer-derived component, water and a humectant and
is substantially free of a water-insoluble polymer having tackiness and a polyvinyl alcohol;
an amount of the water based on a total amount of the layer B is the amount of water based on the total amount of the layer A±10 wt %; and
an amount of the humectant based on the total amount of the layer B is an amount of the humectant based on the total amount of the layer A±10 wt %.

2. The hydrogel according to claim 1, wherein the monomer-derived component in the layer A and the monomer-derived component in the layer B are identical as a compound.

3. The hydrogel according to claim 1, wherein the humectant is a polyhydric alcohol.

4. The hydrogel according to claim 1, wherein adhesive forces of the layer A and the layer B to a phenol-formaldehyde resin plate are 5 to 15 N/20 mm and 0.5 to 7 N/20 mm, respectively.

5. The hydrogel according to claim 1, wherein an intermediate substrate is embedded in the hydrogel having a laminate structure along an in-plane direction.

6. The hydrogel according to claim 5, wherein the intermediate substrate is a semipermeable membrane.

7. A medical-electrode hydrogel to be placed between an electrode constituted of a conductive material and a skin surface when in use, and consisting of the hydrogel according to claim 1, wherein the layer A is a layer in contact with the electrode and the layer B is a layer in contact with the skin surface.

* * * * *